US008449840B2

(12) United States Patent
Saegusa

(10) Patent No.: US 8,449,840 B2
(45) Date of Patent: May 28, 2013

(54) DISPENSING DEVICE

(75) Inventor: Isao Saegusa, Mishima (JP)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 13/001,776

(22) PCT Filed: Mar. 19, 2009

(86) PCT No.: PCT/JP2009/055505
§ 371 (c)(1),
(2), (4) Date: Mar. 25, 2011

(87) PCT Pub. No.: WO2010/001644
PCT Pub. Date: Jan. 7, 2010

(65) Prior Publication Data
US 2011/0171744 A1  Jul. 14, 2011

(30) Foreign Application Priority Data
Jul. 2, 2008  (JP) .................................. 2008 173724

(51) Int. Cl.
*B01L 3/02* (2006.01)
(52) U.S. Cl.
USPC .......... 422/509; 422/501; 422/521; 422/68.1; 422/105; 422/106; 422/107; 436/180
(58) Field of Classification Search
USPC ........ 422/500–501, 509, 521, 68.1, 105–107; 436/180
See application file for complete search history.

(56) References Cited

U.S. PATENT DOCUMENTS

| | | | | | |
|---|---|---|---|---|---|
| 3,800,984 | A | * | 4/1974 | Phelan | 422/509 |
| 4,244,919 | A | * | 1/1981 | Chen | 422/509 |
| 4,277,440 | A | * | 7/1981 | Jessop et al. | 422/509 |
| 4,968,485 | A | * | 11/1990 | Morita | 422/509 |
| 5,447,691 | A | * | 9/1995 | Sanuki | 422/509 |
| 5,882,599 | A | * | 3/1999 | Gilbert | 422/509 |
| 5,916,524 | A | * | 6/1999 | Tisone | 422/509 |

(Continued)

FOREIGN PATENT DOCUMENTS

| | | |
|---|---|---|
| DE | 697 27 422 T2 | 7/2004 |
| EP | 0 810 438 A2 | 12/1997 |

(Continued)

OTHER PUBLICATIONS

Supplementary European Search Report mailed on Feb. 4, 2013 for EP Patent Application No. 097733222.6, 8 pages.

*Primary Examiner* — Brian R Gordon
(74) *Attorney, Agent, or Firm* — Kilpatrick Townsend & Stockton LLP

(57) ABSTRACT

Provided is a dispensing device capable of removing bubbles reliably. In this dispensing device, deaerated water is fed by a water feed pump to the inside of a pipeline up to the vicinity of the leading end of a dispensing nozzle. A water feed valve disposed near a dispensing pump is closed to establish a deaerated water space opened on the leading end side of the dispensing nozzle. The dispensing pump is activated on the space, thereby causing the dispensing nozzle to perform suction and exhaust actions. The dispensing device comprises a vacuum means connected to the space through the water feed valve thereby maintaining a vacuum state. In case the deaerated water space is cleared of the bubbles, the cleared water space is brought, by opening a change-over valve, into communication with a pipeline having a vacuum means connected thereto, thereby bringing the space into the vacuum state.

3 Claims, 10 Drawing Sheets

U.S. PATENT DOCUMENTS

| | | | |
|---|---|---|---|
| 5,927,547 A | 7/1999 | Papen et al. | |
| 6,060,320 A | 5/2000 | Dorenkott et al. | |
| 6,203,759 B1 * | 3/2001 | Pelc et al. | 422/521 |
| 6,579,497 B2 * | 6/2003 | Woodward | 422/66 |
| 6,706,245 B2 * | 3/2004 | Neal et al. | 422/501 |
| 7,198,956 B2 * | 4/2007 | Uffenheimer et al. | 436/180 |
| 7,267,800 B2 * | 9/2007 | Takii et al. | 422/501 |
| 7,288,228 B2 * | 10/2007 | Lefebvre | 422/509 |
| 7,294,309 B1 * | 11/2007 | Goldberg et al. | 422/509 |
| 7,736,591 B2 * | 6/2010 | Rose et al. | 422/502 |
| 2001/0026772 A1 * | 10/2001 | Fuerst et al. | 422/64 |
| 2002/0142341 A1 | 10/2002 | Kameyama et al. | |
| 2002/0159919 A1 * | 10/2002 | Churchill et al. | 422/100 |
| 2003/0207464 A1 * | 11/2003 | Lemmo et al. | 436/180 |
| 2004/0072365 A1 * | 4/2004 | Rose et al. | 436/180 |

FOREIGN PATENT DOCUMENTS

| | | |
|---|---|---|
| EP | 1 391 734 A2 | 2/2004 |
| JP | 60-64256 A | 4/1985 |
| JP | 4-34700 B2 | 6/1992 |
| JP | 10-114394 A | 5/1998 |
| JP | 10-227799 A | 8/1998 |
| JP | 2002-286737 A | 10/2002 |
| JP | 2006-343246 A | 12/2006 |
| JP | 2007-278833 A | 10/2007 |
| JP | 2007-322318 A | 12/2007 |
| WO | WO 01-52991 A1 | 7/2001 |
| WO | 2007/119662 A1 | 10/2007 |

* cited by examiner

DISPENSING DEVICE

CROSS-REFERENCE TO RELATED APPLICATIONS

This application is a National Stage of International Application No. PCT/JP2009/055505, filed Mar. 19, 2009, which claims the benefit of priority to Japanese Application No. 2008-173724, filed Jul. 2, 2008, the disclosures of each are herein incorporated by reference.

TECHNICAL FIELD

The present invention relates to a dispensing device for dispensing a liquid sample containing an analyte or a regent.

BACKGROUND ART

Conventionally, a dispensing device used for dispensing a liquid sample containing an analyte or a regent performs dispensing, by operating a dispensing pump, to discharge a liquid within a tube, for example, to aspirate or discharge the liquid to aspirate a liquid sample from a dispensing nozzle connected to the tube to discharge the aspirated liquid sample to a predetermined position.

However when parts are exchanged for maintenance and the like, in some cases, slight bubbles are mixed into the tube and the bubbles adhere to inside of a cylinder for hosing a liquid or a surface of a plunger which regulates a compression/decompression pressure of the cylinder. In such case, dispensing a liquid sample in the condition where bubbles are adhered causes a variability in the amount of the liquid sample to be dispensed, thereby causing a problem of reducing a dispensing accuracy.

In order to solve this problem, a dispensing device is known that flows a liquid so as to pivot around a plunger in a direction from an injection port of the cylinder to a discharge port of the cylinder to generate a pivotal flow in the cylinder, and removes bubbles adhered inside the cylinder and on the surface of the plunger by the generated pivotal flow (Reference 1).

Reference 1: Japanese Laid-Open Publication No. 2006-343246

DISCLOSURE OF THE INVENTION

Problems to be Solved by the Invention

However, in a dispensing device for removing bubbles by generating a pivotal flow in a liquid within a cylinder, there is a problem that bubbles adhered in a corner of the inside of a cylinder, especially bubbles intruded between a cylinder and a plunger, cannot be removed.

The present invention is made in view of the above, and the purpose of which is to provide a dispensing device capable of steadily removing bubbles.

Means for Solving Problems

To solve the problem mentioned above and to achieve the purpose, a dispensing device of the present invention includes a dispensing pump connected to a tube connecting a dispensing nozzle and a water feed pump; deaerated water supplied into the tube by the water feed pump to fill in the vicinity of a leading end of the dispensing nozzle; a deaerated water space, a leading end of which is open, formed by closing a water feed valve disposed near the dispensing pump; and by operating the dispensing pump for the deaerated water space, performing the suction and exhaust actions by the dispensing nozzle, characterized in that comprising;

a vacuum means for maintaining a negative pressure state connected to the deaerated water space via a change-over valve, when bubbles in the deaerated water space is removed, opening the change-over valve to cause a negative pressure state in the deaerated water space.

Also, in the dispensing device of the present invention above, the water feed valve has a function of a change-over valve and the vacuum means is connected to the water feed valve.

And, in the dispensing device of the present invention above, the vacuum means is filled with the deaerated water preset to a negative pressure.

Effect of the Invention

In the dispensing device according to the present invention, a dispensing pump is connected to a tube connecting a dispensing nozzle and a water feed pump; deaerated water is supplied into the tube by the water feed pump to fill the vicinity of leading end of the dispensing nozzle; a deaerated water space, where a dispensing nozzle's leading end side thereof is open, is formed by closing a water feed valve disposed near the dispensing pump, a vacuum means for maintaining a negative pressure state for the formed deaerated water space via a change-over valve is disposed, when bubble in the deaerated water space are removed, opening the change-over valve to cause a negative pressure state in the deaerated water space, thereby attaining an effect of a volume of bubbles increases to easily remove bubbles in the deaerated water space.

Figure 1:
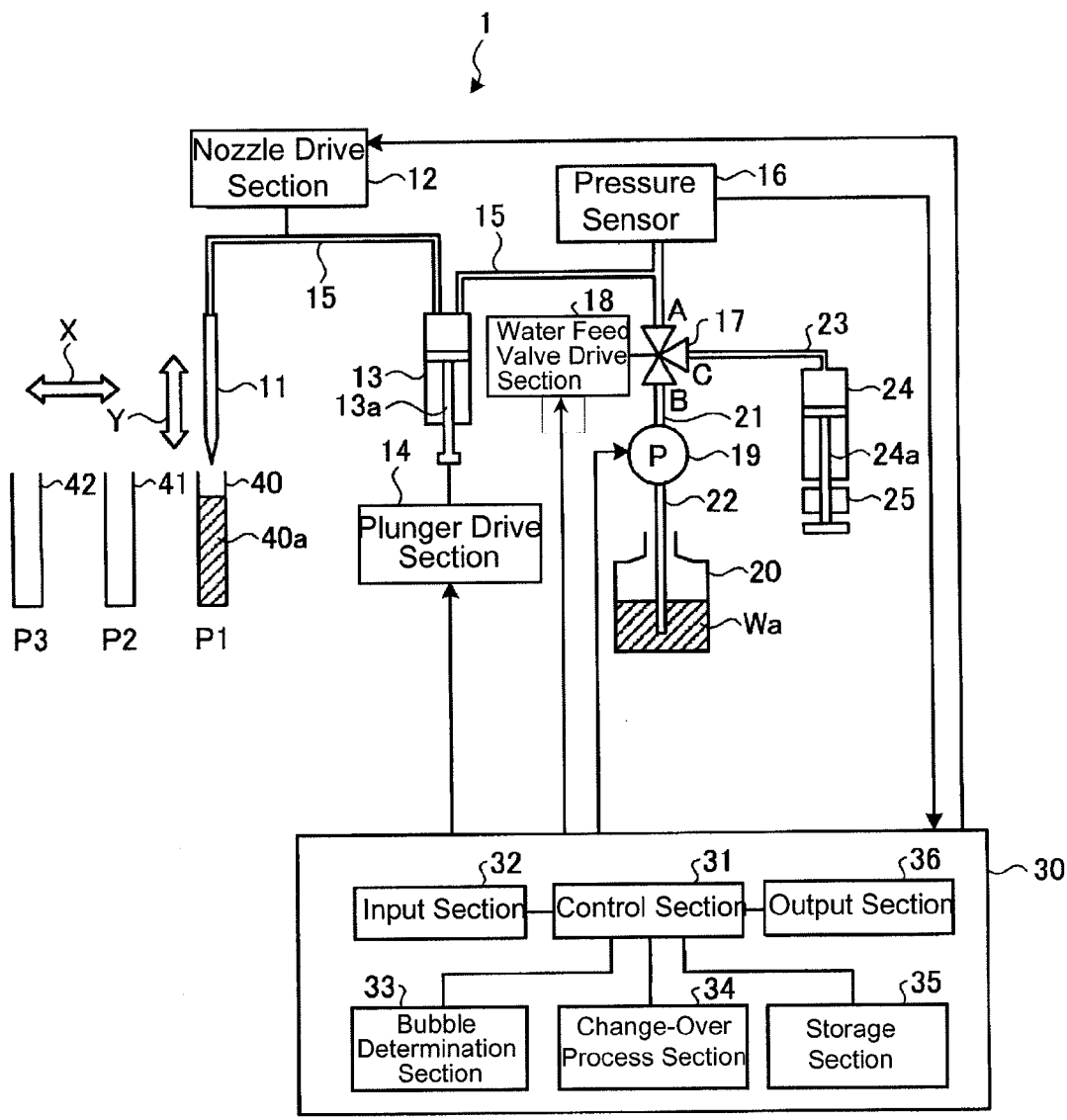
FIG. 1 is a block diagram showing a configuration of a dispensing device according to embodiment 1.

DESCRIPTION OF REFERENCE NUMERALS 1 dispensing device
11 dispensing nozzle 12 nozzle drive section
13 dispensing pump
13a, 24a, 53a plunger
14 plunger drive section
15, 21, 22, 23, 52 tube
16 pressure sensor
17, 50 water feed valve
19 water feed pump
20 tank
24, 53 vacuum means
25, 54 stopper
30 control mechanism
31 control section
32 input section
33 bubble determination section
33a process section
33b detection section
33c calculation section
33d determination section
34, 37 change-over process section
35 storage section
36 output section
40 analyte container
40a analyte
41 reaction chamber
42 cleaning chamber
55 change-over valve drive section
Wa deaerated water

BEST MODE FOR CARRYING OUT THE INVENTION

Hereinafter, a preferable embodiment of a dispensing device according to the present invention will be described with reference to the accompanying figures. Note that the present invention will not be limited to this embodiment. The same numerals are given to identical portions in the description of the figures.

Embodiment 1

FIG. 1 is a block diagram showing the configuration of a dispensing device of embodiment 1 of the present invention. A dispensing device 1 in FIG. 1 performs dispensing, for example, by aspirating a liquid sample containing an analyte or a regent to discharge the aspirated liquid sample. The dispensing device 1 comprises, as shown in FIG. 1, a dispensing nozzle 11, a dispensing pump 13, a pressure sensor 16, a water feed valve 17, a water feed pump 19, a vacuum means 24 and a control mechanism 30.

The dispensing nozzle 11 comprises an object formed in a straight pipe with stainless steel or the like; and moves in a horizontal direction depicted by an arrow X and a vertical direction depicted by an arrow Y in the figure by a nozzle drive section 12. Also, corresponding to the position of position P1, position P2 and position P3, an analyte container 40 containing an analyte 40a, a reaction chamber 41 for discharging the analyte 40a and the cleaning chamber 42 for discharging deaerated water Wa are disposed, respectively.

The dispensing pump 13 is realized with a syringe pump, and operates aspirating and discharging of a plunger 13a by a plunger drive section 14. In addition, the plunger drive section 14 is controlled based on information from the control section 31 to limit the movement of aspirating and discharging of the plunger 13a and the like. And the dispensing pump 13 is connected to the dispensing nozzle 11 and water feed valve 17 by a tube 15.

The pressure sensor 16 detects pressure within the tube 15 to be output to the control section 31 as a pressure signal.

The water feed valve 17 is realized with a three way valve, each port of which is connected to the tube 15 and also to the tube 21 and the tube 23. In more detail, in the water feed valve 17, end A thereof is connected to the tube 15, end B thereof is connected to the tube 21 and end C thereof is connected to the tube 23; and the each end is opened or closed by the water feed valve drive section 18.

The water feed pump 19 aspirates deaerated water Wa stored in the tank 20 to supply the deaerated water Wa into the tube 15 via the water feed valve 17 disposed between the dispensing pump 13 and the water feed pump 19. In addition, the tube 22 is connected to the water feed pump 19; the other end of the tube 22 is connected to the tank 20 for housing the deaerated water Wa. Here, the deaerated water Wa is an incompressible liquid such as deaerated ion exchange water or distilled water or the like.

The vacuum means 24 is realized with a syringe pump to make the pressure of the deaerated water Wa, filled in the tube 15, a negative pressure. The vacuum means 24 fills the deaerated water Wa into the tube 23 to secure a plunger 24a using a stopper 25 realized by a spacer with the completion of aspirating operation of the plunger 24a of the vacuum means 24 for the filled deaerated water Wa. The deaerated water Wa within the tube 23 is set to negative pressure state by the stopper 25.

Next, the control mechanism 30 is explained. The control mechanism 30 comprises a control section 31, an input section 32, a bubble determination section 33, a change-over process section 34, a storage section 35 and an output section 36. The nozzle drive section 12, the plunger drive section 14, the pressure sensor 16, the water feed valve drive section 18, the water feed pump 19 and each section which the control mechanism 30 comprises are connected to the control section 31.

The control section 31 is realized by a CPU to control processing and operation of each section of the dispensing device 1. The control section 31 performs predetermined input/output control for information input into each of these components, and performs predetermined information processing for the information.

The input section 32 is realized with a keyboard, a mouse and a touch panel comprising an input/output function and the like to obtain instruction information or the like required for dispensing an analyte from outside. In addition, the input section 32 obtains instruction information for the control section 31 via a communication network (not shown) to transmit the information.

The bubble determination section 33 detects pressure within the tube 15 based on a pressure signal output from the pressure sensor 16 to determine the existence of bubbles within the tube 15 based on the detected pressure waveform.

The change-over process section 34 controls the water feed valve drive section 18 via the control section 31 based on the information which an operator inputs to the input section 32 to perform an open/close operation of the water feed valve 17 and an change-over process of the tube connection.

The storage section 35 is realized by a hard disk for magnetically storing information and a memory for loading from the hard disk and for electrically storing various programs required for processing when the dispensing device 1 performs the processing. In addition, the storage section 35 may comprise an auxiliary storage device capable of reading the stored information on storage medium such as CD-ROM, DVD-ROM, PC card or the like.

The output section 36 is realized with a display, a printer, a speaker and the like to output various information. The output section 36 outputs the existence of bubbles within the tube 15 when the bubble determination section 33 determines there are bubbles within the tube 15.

Thus configured dispensing device 1 supplies deaerated water Wa from the tank 20 by the water feed pump 19 under control of the control section 31 to fill a space from between the dispensing nozzle 11 to the water feed valve 17 with deaerated water Wa. Then, the dispensing device 1 closes the water feed valve 17 and operates exhaust of the plunger 13a by the plunger drive section 14 to discharge the predetermined amount of deaerated water Wa to the cleaning chamber 42 disposed at position P3. Afterwards, by aspirating and exhausting the plunger 13a with the plunger drive section 14, the dispensing device 1 aspirates the analyte 40a within the analyte container 40 disposed at position P1 to discharge the analyte 40a to the reaction chamber 41 disposed at position P2. Thereby a series of dispensing operation for dispensing one analyte 40a from the analyte container 40 to the reaction chamber 41 is completed. In addition, when the analyte 40a is aspirated or discharged at the leading end portion of the dispensing nozzle 11, since an air layer exists between the analyte 40a and the deaerated water Wa, the analyte 40a is not mixed with deaerated water Wa.

Next, when the dispensing pump 13 is exchanged in the dispensing device 1, for example for maintenance and the like, bubbles may exist within the tube 15 filled with deaerated water Wa. In such a case, the change-over process section 34 opens end A and end C of the water feed valve 17 by driving the water feed valve drive section 18 to change-over the tube 15 and tube 23 in a communication state. By this change-over, the deaerated water Wa of negative pressure filled in the vacuum means 24 cause a pressure applied to the deaerated water Wa filled in the tube 15 to be negative, thereby the deaerated water Wa is caused to backflow in the reverse direction of the dispensing nozzle 11. Due to this reverse flow, a volume of bubbles increases due to the negative pressure, and the bubbles adhered to the dispensing pump 13 are easily removed. Afterwards, the bubbles removed from the dispensing pump 13 are discharged from the dispensing nozzle 11 with deaerated water Wa supplied by the water feed pump 19, thereby, the bubbles within the tube 15 are removed.

Figure 2:
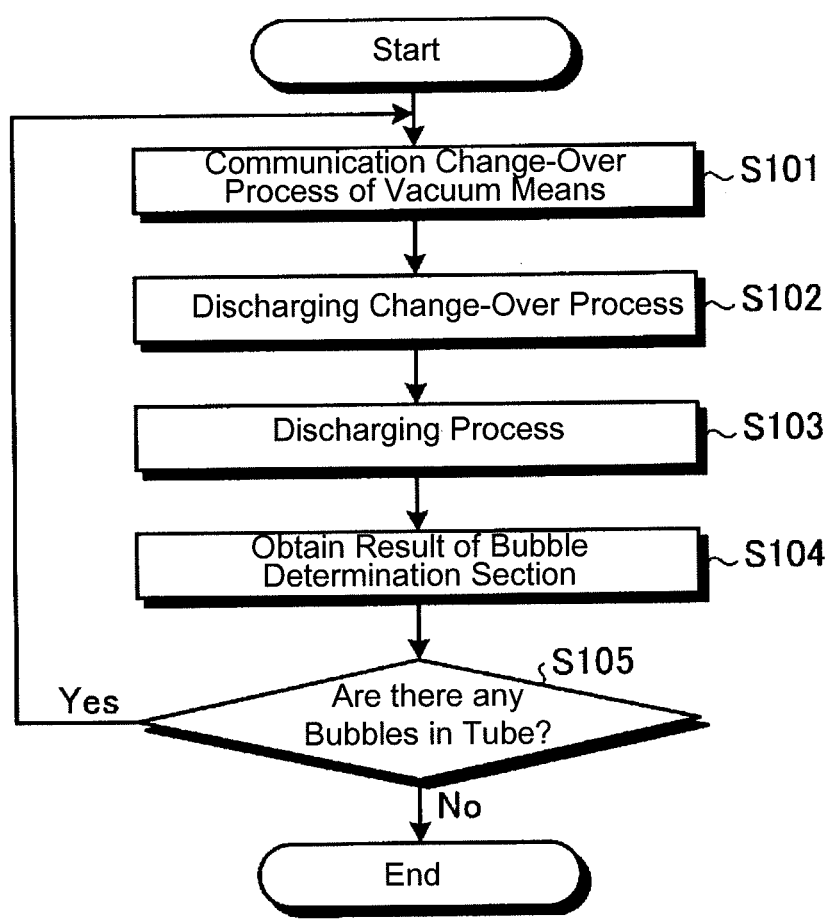
FIG. 2 is a flow chart showing a change-over procedure by a change-over process section of embodiment 1.

Referring now to the flow chart depicted in FIG. 2, a change-over process procedure performed by a change-over process section 34 is explained for the case removing bubbles within the tube 15. In FIG. 2, first, the change-over process section 34 drives the water feed valve drive section 18 based on information which an operator input into an input section 32 via a control section 31 to open end A and end C from the state where each of end A, end B and end C of the water feed valve 17 are closed, thereby performing a change-over to make the tube 15 and the tube 23, to which the vacuum means 24, connected in communication state (step S101). Thereby as mentioned above, a negative pressure state of the vacuum means 24 acts inside the tube 15.

Afterwards, the change-over process section 34 closes the end C of the water feed valve 17 via the water feed valve drive section 18 and opens the end B to perform a change-over for setting the tube 15 and tube 21 in communication state (Step S102).

Then, the water feed pump 19 is driven to supply deaerated water Wa into the tube 15, and a discharge process for discharging removed bubbles with deaerated water Wa from the dispensing nozzle 11 is performed (Step S103).

Subsequently, the change-over process section 34 obtains the determination result made by the bubble determination section 33 via the control section 31 (Step S104) to determine whether or not the bubble determination section 33 has determined there are bubbles in the tube 15 (Step S105). If the bubble determination section 33 determines there are bubbles in the tube 15 (Step S105: Yes) the process is returned to Step S101, and repeat a process of change-over and discharging with Step S101 to Step S104 mentioned above until it is determined that no bubbles exist in the tube 15. On the other hand, when the bubble determination section 33 determines there are no bubble in the tube 15 (Step S105: No), the present process ends.

Embodiment 1 can reliably remove bubbles introduced into the tube 15 with a simple configuration that comprises a vacuum means 24 for keeping a negative pressure state in the tube 15 via water feed valve 17 to act as the negative pressure state of the vacuum means 24 to the tube 15.

Embodiment 2

Next, the embodiment 2 of the present invention is explained. In the embodiment 1 mentioned above, the vacuum means 24 is connected to inside of the tube 15 via the water feed valve 17; however, in the embodiment 2 of the present invention, a vacuum means 53 is connected to the tube 15 via the change-over valve 51.

Figure 3:
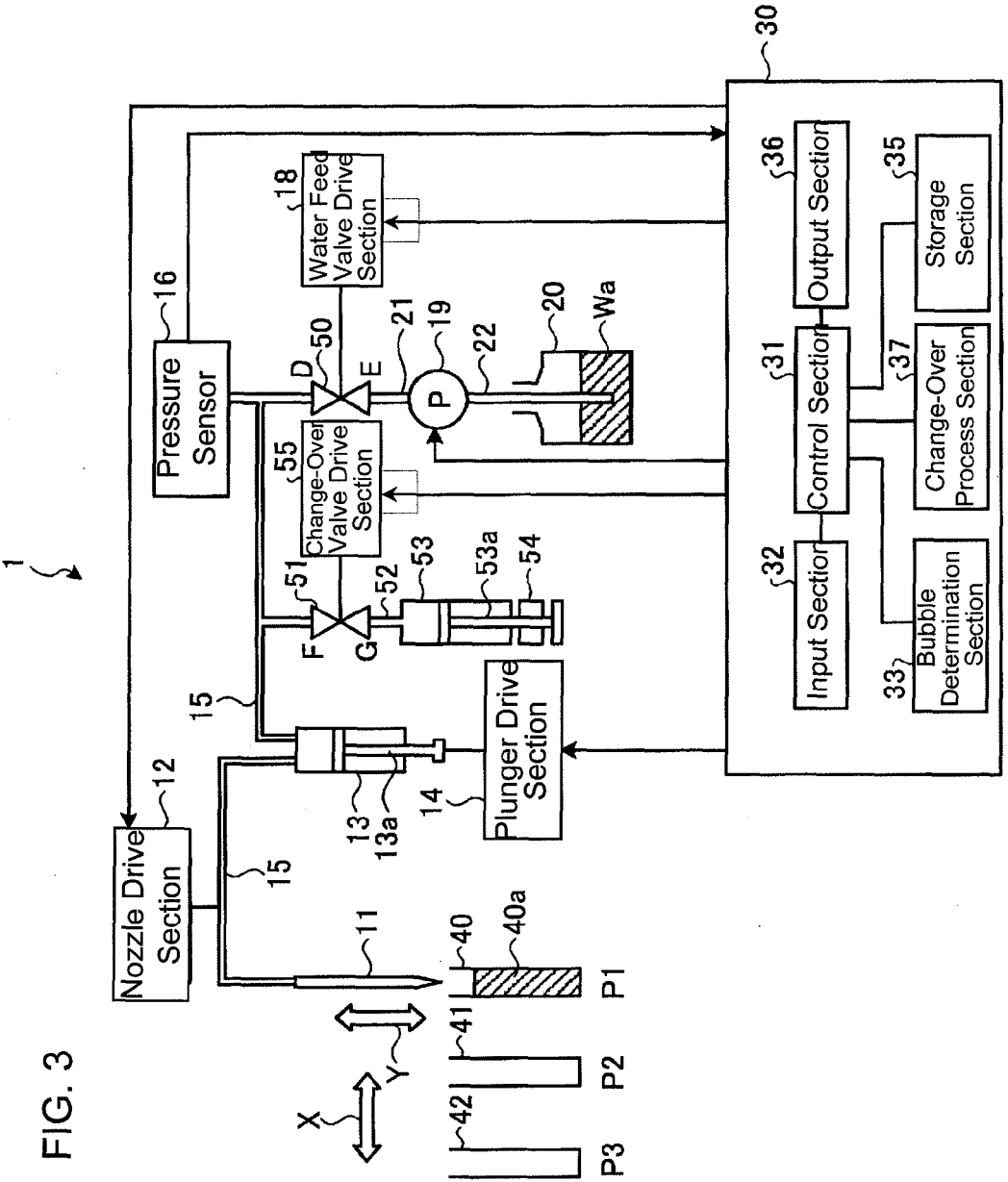
FIG. 3 is a block diagram showing a configuration of a dispensing device according to embodiment 2.

FIG. 3 is a block diagram showing a configuration of the dispensing device of the embodiment 2 of the present invention. As shown in FIG. 3, in this embodiment 2, a vacuum means 53 similar to that of embodiment 1 is connected between a dispensing pump 13 and a water feed valve 50 to the tube 15 via a change-over valve 51, and the negative pressure state of this vacuum means 53 acts inside the tube 15. The change-over valve 51 is realized with an electro-magnetic valve and is connected to the tube 15 and to a tube 52. In more detail, end F of the change-over valve 51 is connected to the tube 15, and end G of the change-over valve 51 is connected to the tube 52. In addition, the water feed valve 50 is realized with an electro-magnetic valve, end D of the water feed valve 50 is connected to the tube 15 and end E of the water feed valve 50 is connected to a tube 21. Also a change-over process section 37 controls a water feed valve drive section 18 and a change-over valve drive section 55, based on information which an operator inputs to an input section 32 via a control section 31, to perform an open/close operation of the water feed valve 50 and the change-over valve 51 and a connection change-over process for tubes.

Figure 4:
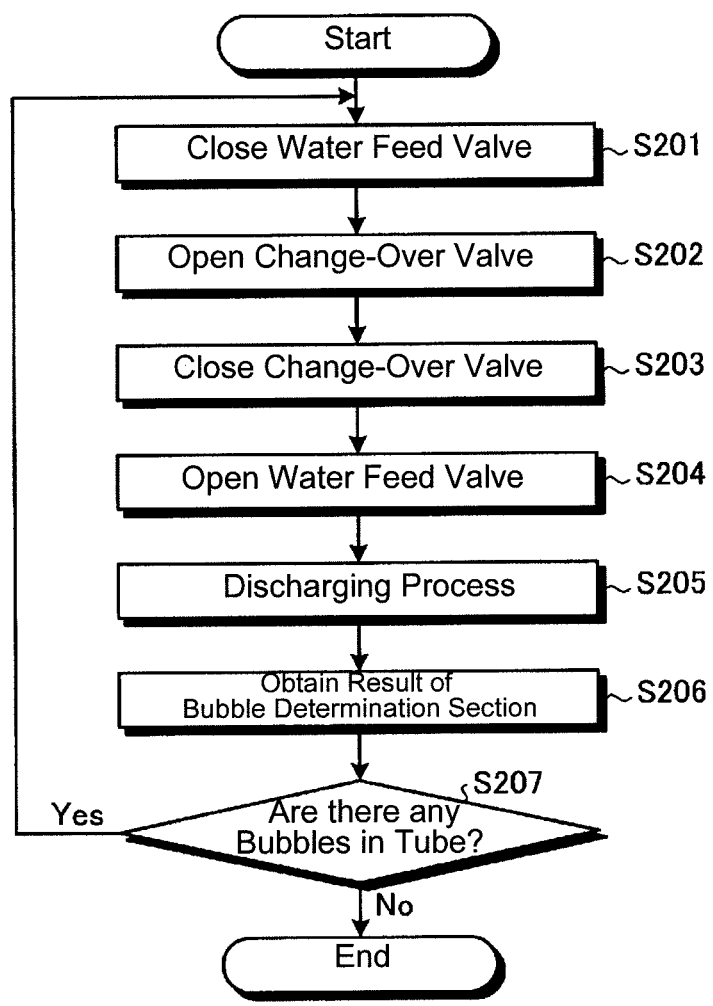
FIG. 4 is a flow chart showing a change-over procedure by a change-over process section of embodiment 2.

Now, referring to the flow chart shown in FIG. 4, a change-over process procedure with the change-over process section 37 in the case of removing bubbles from the tube 15 is explained. In FIG. 4, first, based on information which an operator input to the input section 32 via the control section 31, the change-over process section 37 drives the water feed valve drive section 18 to close a valve of the water feed valve 50 (Step S201), and drives the change-over valve drive section 55 to open a valve of the change-over valve 51 and to change-over the tube 15 and tube 52 to which the vacuum means 53 is connected to a communication state (Step S202). By this change-over, a negative pressure state of the vacuum means 53 acts inside the tube 15.

Subsequently, the change-over process section 37 drives the change-over valve drive section 55 to close a valve of the change-over valve 51 (Step S203), and drives the water feed valve drive section 18 to open a valve of the water feed valve 50 and to change-over the tube 15 and the tube 21 to the communication state (Step S204).

Then, the water feed pump 19 is driven to supply deaerated water Wa into the tube 15, and a discharge process is performed for discharging peeled bubble with deaerated water Wa from the dispensing nozzle 11 (Step S205).

Subsequently, the change-over process section 37 obtains the determination result made by the bubble determination section 33 via the control section 31 (Step S206) to determine whether or not the bubble determination section 33 has determined if there are bubbles in the tube 15 (Step S207). If the bubble determination section 33 determines there are bubbles in the tube 15 (Step S207: Yes), then the process is returned to Step S201, and a process of change-over and discharging between Step S201 and Step S206 mentioned above, is repeated until it is determined that no bubbles exist in the tube 15. On the other hand, when the bubble determination section 33 determines there are no bubbles in the tube 15 (Step S207: No), the present process ends.

In embodiment 2, since the vacuum means 53 can connect to the tube 15 via the change-over valve 51 without fixing a connecting position of the vacuum means 53, in addition to an increase in a freedom of design of the dispensing device 1, bubbles existing in the tube 15 can be surely removed.

Figure 5:
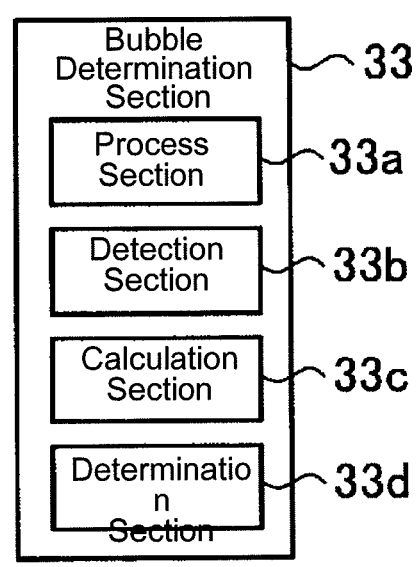
FIG. 5 is a block diagram showing a configuration of a bubble determination section.

Now, the bubble determination section 33 used in the embodiments 1 and 2 mentioned above is explained in detail. As shown in FIG. 5, the bubble determination section 33 has a process section 33a, a detection section 33b, a calculation section 33c and a determination section 33d. The process section 33a amplifies a pressure signal output from a pressure sensor 16; based on the amplified pressure signal, performs a conversion process to a digital signal, and is specifically realized by an A/D converter. The detection section 33b detects a pressure in the tube 15 from the pressure signal converted to the digital signal by the process section 33a. The calculation section 33c calculates a slope of each pressure waveform where the pressure waveform indicated by the pressure signal detected by the detection section 33b is divided into a plurality of sections along the time axis. The determination section 33d determines the existence of bubbles in the tube 15 based on the number of sections where the slope calculated by the detection section 33b is outside of a range of a prescribed slope for the absence of bubbles.

Figure 6:
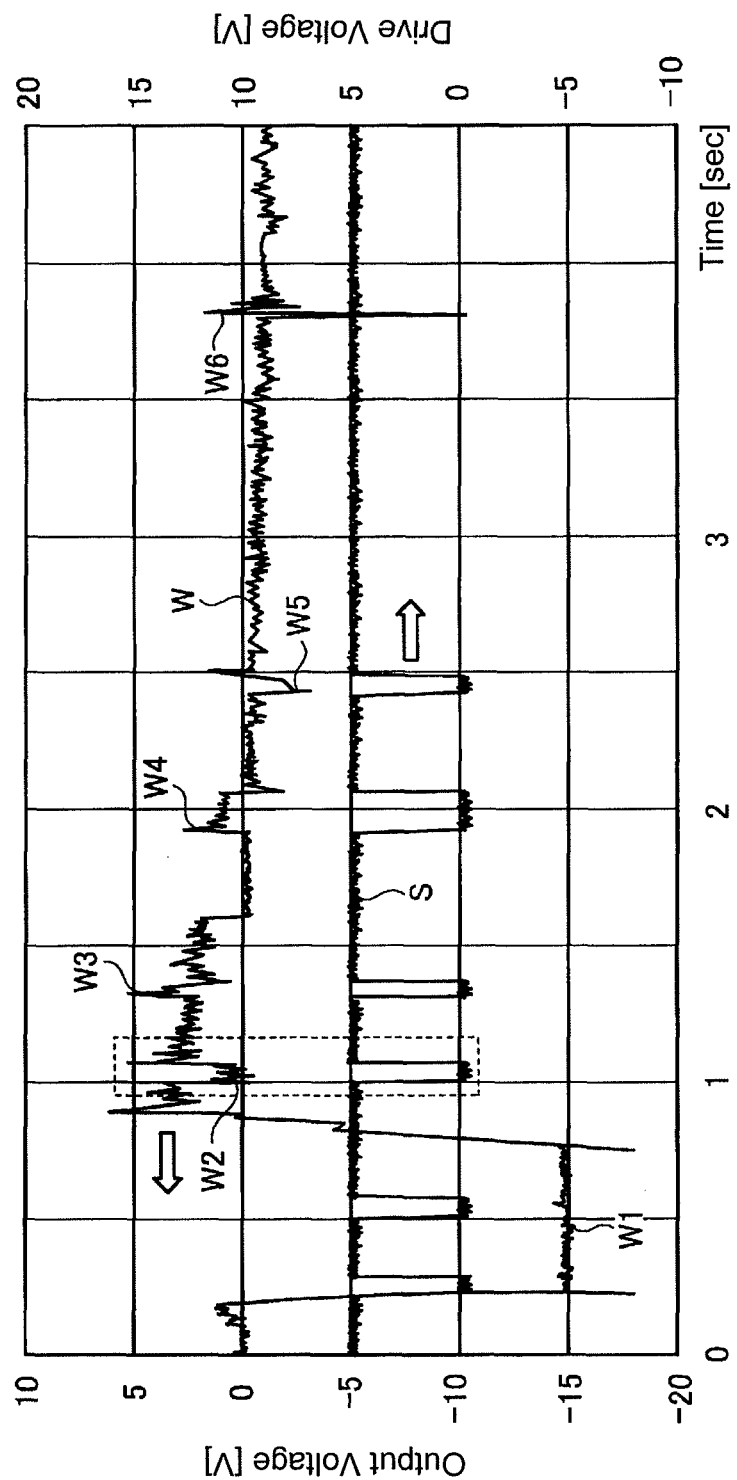
FIG. 6 is a figure of a waveform showing a pressure waveform of deaerated water in a tube detected by a pressure sensor.

Next, referring to FIG. 6, a pressure waveform inside the tube 15 detected by the pressure sensor 16 is explained. This pressure waveform W is a pressure variation within the tube 15 indicated by an output voltage of the pressure sensor 16 when the dispensing device 1 dispenses analytes. In FIG. 6, a transverse axis indicates time (sec.); a left vertical axis indicates an output voltage (V) of a pressure signal output by the pressure sensor 16; and a right vertical axis indicates drive voltage (V) of drive signal S driving a plunger 13a within a dispensing pump 13 output to the plunger drive section 14 from the control section 31.

As shown in FIG. 6, the pressure waveform W sequentially represents a pressure waveform W1 for cleaning the inside of the dispensing nozzle 11, a pressure waveform W2 for discharging deaerated water Wa, a waveform W3 when the predetermined amount of air is aspirated into a leading end of the dispensing nozzle 11, a waveform W4 when the predetermined amount of analyte is aspirated into the dispensing nozzle 11, a waveform W5 when discharging an excess amount in the dispensing nozzle 11 which is aspirated to an analyte container 40 is slightly more than the required amount for analysis, and a waveform W6 when discharging an aspirated analyte in the dispensing nozzle 11 to a reaction chamber 41.

Figure 7:
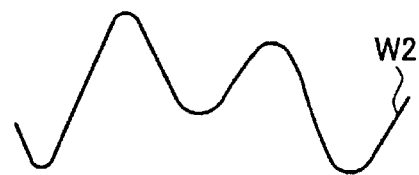
FIG. 7 is an enlarged schematic diagram of a pressure waveform when no bubbles exist in deaerated water in a tube.
Figure 7:
Figure 8:
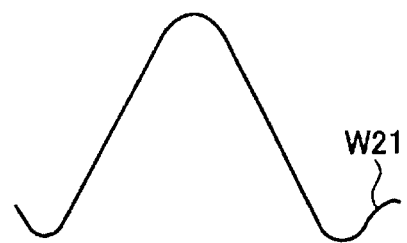
FIG. 8 is an enlarged schematic diagram of a pressure waveform when many bubbles exist in deaerated water in the tube.
Figure 8:
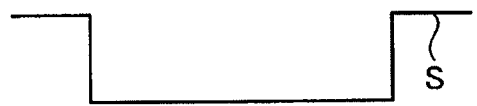

Here, FIG. 7 is a schematically enlarged pressure waveform W2 and depicts the case where bubbles do not exist in the deaerated water Wa in the tube 15. In this case, two large peaks are formed in a waveform. On the contrary, if bubbles exist in the deaerated water Wa, since the pressure transfer rate is reduced by bubbles, the pressure variation slows; therefore, the pressure waveform W2 forms only one large peak as in waveform W21 as shown in FIG. 8. The pressure waveform W21 depicted in the figure represents the case when the amount of bubbles residing in the deaerated water Wa is large; a waveform approaches pressure waveform W2 shown in FIG. 7 as the amount of bubbles decreases.

Figure 9:
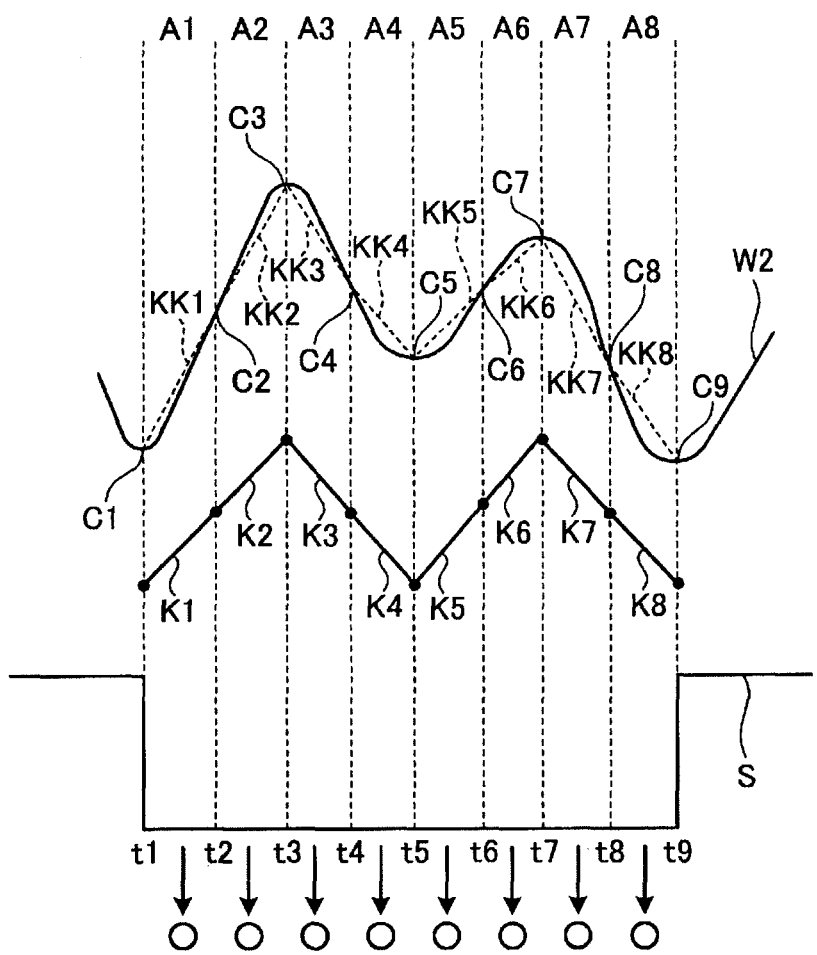
FIG. 9 is an explanation figure for explaining a determination process when no bubbles exist in deaerated water in a tube.

Therefore, in this bubble determination section 33, as shown in FIG. 9, an interval of the pressure waveform W2 is divided into a plurality of sections A1-A8, then in each interval A1-A8, by comparing reference slopes K1-K8 of the waveform W2 without bubbles and slope of each interval of the pressure waveform detected by the pressure sensor 16, and the number of intervals is counted when the slope of each interval exceeds a predetermined slope range of the each reference slope K1-K8; if the count value is one or more, it is determined that bubbles exist in the tube 15.

Specifically, as shown in FIG. 9, intervals A1-A8 are set, divided by predetermined sampling time point t1-t9 corresponding to a pressure waveform W2 where bubbles do not exist, and reference slope k1-K8 of each interval A1-A8 are set which correspond to a pressure waveform W2 where bubbles do not exist. These sampling time points t1-t9 are preferred, for example, to correspond to a relative maximum point or a relative minimum point of the pressure waveform W2. The pressure signal obtained by the pressure sensor 16 is converted to digital pressure voltage value by the process section 33a, and the detection section 33b detects pressure voltage values C1-C9 for each sampling time point t1-t9, and the calculation section 33c calculates slopes KK1-KK8 of each interval A1-A8. For example, slope KK1 of interval A1 is calculated by the equation $KK1=(C2-C1)/(t2-t1)$.

Figure 10:
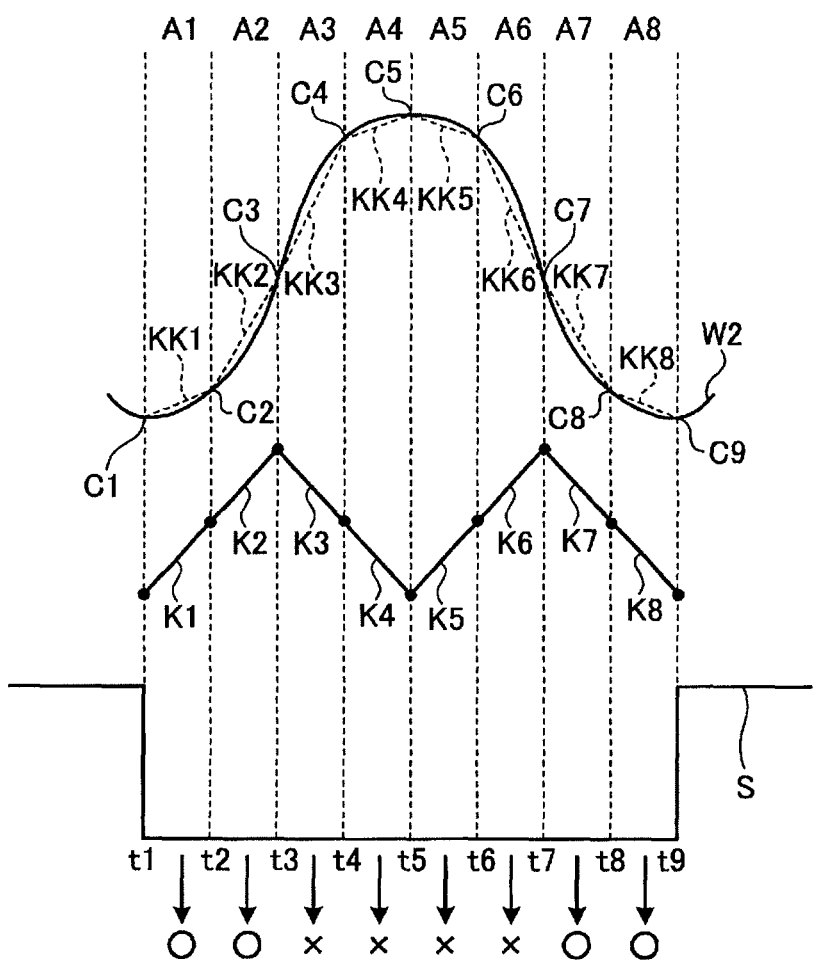
FIG. 10 is an explanation figure for explaining a determination process when many bubbles exist in deaerated water in the tube.

The determination section 33d subtracts each reference slope K1-K8 from each slope KK1-KK8; if the subtraction result is within a predetermined absolute value, a determination of "○" is made; and if the subtract result is outside a predetermined absolute value, a determination of "x" is made. When the number of determined "x" are one or more, it is determined that there are bubbles in the tube 15. For example, in FIG. 9, all the intervals A1-A8 are determined as "○"; therefore, the determination is output that bubbles do not exist in the tube 15. On the other hand, in FIG. 10, the determinations of intervals A3-A6 are "x", then since the determined "x" are one or more, the determination is output that bubbles exist in the tube 15.

Figure 11:
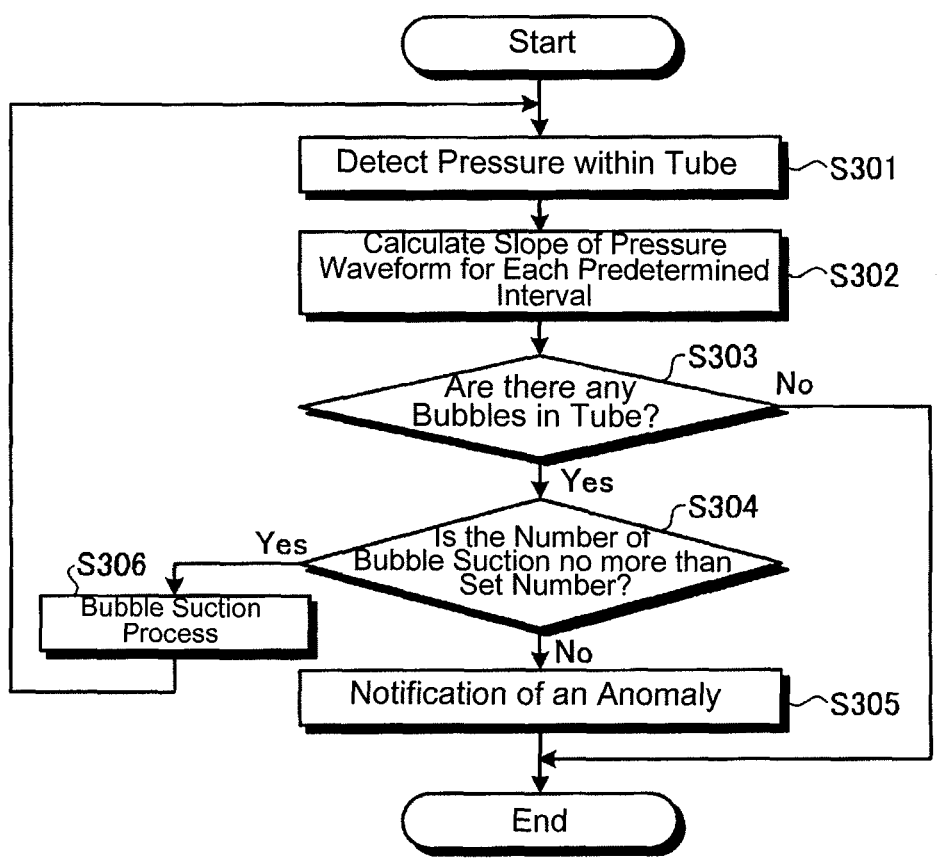
FIG. 11 is a flow chart showing a determination process procedure of existence or nonexistence of bubbles in a tube by a bubble determination section.

Here, referring to the flowchart shown in FIG. 11, a determination process procedure to determine the existence of bubbles within the tube 15 by a bubble determination section 33 is explained. In FIG. 11, first, the dispensing device 1 drives a dispensing pump 13 under control of a control section 31 when checking prior to starting the dispensing of the setup of an analysis device, and discharges deaerated water Wa to a cleaning chamber 42 at point P3 from a dispensing nozzle 11 the inside of which has already been cleaned. In this case, the process section 33a converts a pressure waveform detected by the pressure sensor 16 to digital signal, and a detection section 33b detects a pressure waveform based on the converted digital signal (Step S301).

Subsequently, the calculation section 33c calculates each slope of each interval A1-A8 based on the pressure waveform detected by the detection section 33b (Step S302). Then, the determination section 33d compares each slope KK1-KK8 calculated for each interval A1-A8 and the pre-obtained reference slope K1-K8 where no bubbles exist; based on the number of intervals where the slopes KK1-KK8 are outside a predetermined range from the pre-obtained reference slope K1-K8, the existence of bubbles in the tube 15 is determined (Step S303). Specifically, if the number of intervals in which slopes KK1-KK8 are outside of a predetermined range is one or more, it is determined that bubbles exist in the tube 15. If it is determined there are no bubbles (Step S303: No), the present process ends. In this case, the determination section 33d may output a display or the like indicating there are no bubbles in the tube 15 to the output section 36 via the control section 31. At completion of this determination process, the dispensing device 1 starts the dispensing of a liquid sample containing an analyte or a regent.

On the other hand, if it is determined that bubbles exist (Step S303: Yes), the determination section 33d determines whether the number of bubble sections is less than a set number or not (Step S304). If the number of bubble sections is more than or equal to the set number (Step S304: No), it is the case that bubbles are mixed in the tube 15 in spite of a bubble suction operation, therefore the process is transferred to Step S305 to notify of an anomaly (Step S305), then the determination section 33d outputs a display or the like indicating there are bubbles in the tube 15 to the output section 36 via the control section 31.

On the contrary, if the number of bubble sections is no more than the predetermined number (Step S304: Yes), the bubble suction process is performed (Step S306). This bubble suction process is performed by outputting a control signal to the water feed valve drive section 18 to open a valve, and driving the water feed pump 19 to supply deaerated water Wa in a tank 20 to the tube 15. With this bubble suction process, bubbles existing in the tube 15 are discharged with deaerated water Wa to a cleaning chamber 42. And then, the determination section 33d returns to Step S301 to repeat the aforementioned determination process for the existence of bubbles in the tube 15.

Since the bubble determination section 33 is necessary only to detect the pressure inside the tube 15 using the pressure sensor 16, it is easily determined that bubbles exist in the tube 15 before dispensing. As a result, time for performing a re-inspection and the like due to dispensing with a low accuracy can be shortened; thereby a reduction in analysis time is obtained.

In addition, the bubble determination section 33 determines the existence of bubbles in the tube 15 when the number of "x" determinations is one or more; however, without restriction to this, depending on the amount of the difference between a pressure waveform where bubbles exist and a pressure waveform where no bubble exists, the number of determined "x" may be varied.

In addition, this bubble determination section 33 sets a predetermined slope range for determining "○" or "x"; however, instead of the slope range, it may be determined depending on whether a slope of each interval A1-A8 is positive or negative. For example, assuming the reference slope K1 of the interval A1 is "positive", if the slope KK1 is "positive"; then the determination "○" is made, and if the slope KK1 is "negative"; then the determination "x" is made. Thereby, a determination process by the determination section 33 is simplified.

Also in this bubble determination section 33, the intervals A1-A8 have the same time interval; however, without restriction to this, the time intervals of each interval A1-A8 may be different according to a pressure waveform where no bubbles exist.

Also in this bubble determination section 33, a determination of the existence of bubbles is performed based on a pressure waveform W2 when deaerated water Wa is discharged; however, without restriction to this, a determination of the existence of bubbles may be performed based on another pressure waveform within the tube 15.

Now, in the embodiments 1 and 2 mentioned above, it is preferable after causing a pressure applied to deaerated water Wa in the tube 15 to be negative, an operator detaches a stopper 25 or stopper 54 then moves a plunger 24a or plunger 53a to perform suction and exhaust actions. By performing the suction and exhaust actions, since deaerated water Wa moves within the tube 15, bubbles adhered inside the tube 15 and the dispensing pump 13 and the volume of which have increased, can be reliably removed to deaerated water Wa.

In addition, in the embodiments 1 and 2 mentioned above, it is preferable to fix a plunger 13a when the inside of the tube 15 is to be negative pressurized by the vacuum means 24 or a vacuum means 53. By fixing the plunger 13a, the negative pressure within the tube 15 and the dispensing pump 13 can be ensured.

Also in embodiments 1 and 2 mentioned above, when dispensing is restarted after stopping the dispensing operation for a long time, since bubbles may exist within the tube due to an environmental temperature, the atmospheric pressure, a tiny leak or the like, it is preferable to perform the bubble removing process mentioned above when the dispensing is restarted.

INDUSTRIAL APPLICABILITY

As described above, the dispensing device of the present invention is useful to reliably remove bubbles.

The invention claimed is:

1. A dispensing device, comprising:
   a dispensing nozzle comprising a leading end;
   a water feed pump;
   a water feed valve;
   a tubing;
   a change-over valve separate from the water feed valve;
   a vacuum means;
   a dispensing pump connected to the tubing, wherein the tubing is disposed between the dispensing nozzle and the water feed pump;
   wherein the vacuum means is separate from the water feed pump and the dispensing pump;
   wherein the water feed pump is configured to supply deaerated water into the tubing to fill up the tubing to the leading end of the dispensing nozzle;
   wherein the water feed valve is configured to be closed thereby forming a deaerated water space in the tubing, where the leading end of the dispensing nozzle is open, wherein the deaerated water space is between the dispensing nozzle and the water feed valve;
   wherein the dispensing pump is separate from the water feed pump and is configured to be operated to perform a suction and an exhaust action using the dispensing nozzle,
   wherein the vacuum means is configured to maintain a negative pressure state in the tubing via the change-over valve;
   wherein the vacuum means is connected to the deaerated water space via the change-over valve; and
   wherein the change-over valve is configured to be opened such that the vacuum means negatively pressurizes the deaerated water space such that bubbles in the deaerated water supplied to the deaerated water space are removed;
   wherein the dispensing device further comprises control circuitry programmed to cause the change-over valve to repeatedly open to remove bubbles in the deaerated water, until the control circuitry determines that no bubbles exist in the deaerated water space.

2. The dispensing device according to claim 1 wherein the vacuum means is configured to cause additional tubing, which is connected to the vacuum means, to be filled with the deaerated water such that the vacuum means can negatively pressurize the deaerated water.

3. A dispensing device, comprising:
a dispensing nozzle comprising a leading end;
a water feed pump;
a water feed valve;
tubing;
a vacuum means;
a dispensing pump connected to the tubing, wherein the tubing is disposed between the dispensing nozzle and the water feed pump;
wherein the vacuum means is separate from the water feed pump and the dispensing pump;
wherein the water feed pump is configured to supply deaerated water into the tubing to fill up the tubing to the leading end of the dispensing nozzle;
wherein the water feed valve is configured to be closed thereby forming a deaerated water space in the tubing, where the leading end of the dispensing nozzle is open, wherein the deaerated water space is at least between the dispensing nozzle and the water feed valve;
wherein the dispensing pump is separate from the water feed pump and is configured to be operated to perform a suction and an exhaust action using the dispensing nozzle,
wherein the vacuum means is configured to maintain a negative pressure state in the tubing via the water feed valve;
wherein the vacuum means is connected to the deaerated water space via the water feed valve; and
wherein the water feed valve is configured to be opened such that the vacuum means negatively pressurizes the deaerated water space such that bubbles in the deaerated water supplied to the deaerated water space are removed, wherein the vacuum means is connected to the water feed valve;
wherein the dispensing device further comprises control circuitry programmed to cause the water feed valve to repeatedly open to remove bubbles in the deaerated water space, until the control circuitry determines that no bubbles exist in the deaerated water space.

* * * * *